United States Patent
Stevens et al.

(10) Patent No.: US 6,217,542 B1
(45) Date of Patent: Apr. 17, 2001

(54) TAMPON INSERTION DEVICE

(75) Inventors: Tiffany April Stevens; Chrissie Melinda Smits; Melvin Cecil Wilson, Jr.; Adrienne Michelle Szmuriga, all of Cincinnati, OH (US)

(73) Assignee: The Procter & Gamble Company, Cincinnati, OH (US)

(*) Notice: Subject to any disclaimer, the term of this patent is extended or adjusted under 35 U.S.C. 154(b) by 0 days.

(21) Appl. No.: 09/398,270

(22) Filed: Sep. 17, 1999

(51) Int. Cl.[7] ............................................. A61F 13/20
(52) U.S. Cl. ........................................................... 604/17
(58) Field of Search ................................ 604/11–18, 904, 604/285–288, 57–60

(56) References Cited

U.S. PATENT DOCUMENTS

| 2,711,173 | * | 6/1955 | Seidler | 604/14 |
| 2,879,770 | * | 3/1959 | Graham, Jr. | 604/14 |
| 3,103,929 | * | 9/1963 | Brecht | 604/904 |
| 3,424,159 | * | 1/1969 | Whitehead et al. | 604/904 |
| 3,575,169 | * | 4/1971 | Voss | 604/14 |
| 3,831,605 | * | 8/1974 | Fournier | 604/288 |
| 4,822,332 | * | 4/1989 | Kajander | 604/15 |
| 4,881,644 | * | 11/1989 | Norquest et al. | 604/16 |

* cited by examiner

Primary Examiner—Dennis Ruhl
(74) Attorney, Agent, or Firm—Theodore P. Cummings; Matthew P. Fitzpatrick; Kevin C. Johnson

(57) ABSTRACT

The invention provides a tampon insertion device comprising a tampon applicator having a first end and a second end, a tampon having a string, the tampon being positioned within the tampon applicator, and a plunger attached to the tampon applicator by the tampon string. The string is attached to the plunger at at least one connection point on the plunger. The tampon applicator with the tampon therein and the plunger are preferably positioned adjacent to one-another in a substantially parallel orientation prior to the use of the tampon insertion device. Such parallel orientation between the tampon applicator and the plunger is maintained by the tampon string connected to the plunger.

4 Claims, 4 Drawing Sheets

TAMPON INSERTION DEVICE

FIELD OF THE INVENTION

The invention provides miniature tampon insertion devices, generally a tampon applicator and a plunger in a folded configuration prior its use.

BACKGROUND OF THE INVENTION

Most commercially available tampon applicators for introducing catamenial tampons intravaginally consist of a pair of telescoping tubes. The tampon applicator is designed to store a tampon therein at one end. Typically, the plunger is slightly smaller in diameter and is slidably positioned behind the tampon carried in the tampon applicator. In use, the tampon is ejected from the tampon applicator by pushing the plunger into the tampon applicator to expel the tampon.

Several drawbacks are associated with such applicators for certain uses. First, the tampon applicator must be of length sufficient to assure proper depth of insertion. For example, such tampon applicators are substantially longer than the tampons. Next, when the tampon and tampon applicator are assembled with the plunger, a major portion of the plunger necessarily extends out from the end of the tampon applicator. This results in the over-all length of the packaged ready-for-use tampon applicator being approximately two and one-half times the length of the tampon. As a result of such a relatively large size, the bulk and cost of the packaging for such applicators are often greatly increased.

Women commonly carry such packaged tampons (with applicators) in their purses. Because of the length of such applicators, they occupy a relatively large amount of space in the purse. It is therefore also desirable to produce a tampon applicator of smaller or compact size which is less obtrusive. This is a particular problem for younger women who often prefer not to carry purses and with today's fashions often must use pockets in relatively tight-fitting clothing.

One type of tampon applicator which has been proposed to solve the above problems utilizes a substantially flat, elongated plunger arm which is stored positioned along the outside of and in longitudinal alignment with the tampon applicator. For example, please see U.S. Pat. Nos. 2,222,088; 3,059,641; 3,059,642; 3,103,929; 3,115,876; 3,424,159; 3,759,258; 3,831,605; and 4,269,187.

Another type of tampon applicator has been proposed to solve the foregoing problems of telescoping the plunger completely into the tampon applicator while storing the tampon completely in the tampon applicator while storing the tampon in the distal end of the plunger. This also shortens the tampon and applicator assembly by the length of a tampon. Operatively, the plunger is then drawn out most of the way from the proximal end of the tampon applicator leaving behind the tampon until the distal end of the plunger can engage the proximal end of the stored tampon. Each patentee discloses a different way of securing the stored tampon in the distal end of the tampon applicator to prevent proximal displacement end of the tampon while the plunger is withdrawn therefrom. See U.S. Pat. No. 3,101,713; British Patent No. 2,033,754; U.S. Pat. Nos. 2,832,342 (distal end of withdrawal string secured to slot in distal of tampon applicator); U.S. Pat. No. 3,090,385 (having an ejector arm, rather than an plunger); U.S. Pat. No. 4,276,881; 4,286,595; 4,411,647 and 4,479,791.

Apparently, none of the foregoing types of applicators has ever been commercially successful.

In the field of compact tampon applicator embodiments have been created which have attempted to accommodate consumer's needs for economy of space in packaging. For example, U.S. Pat. Nos. 4,726,805, 4,846,802; and 4,960,417 provide compact tampons wherein the plunger is packaged in a substantially inserted position within the tampon applicator itself Upon use, a user retrieves the embodiment from the package and then extends the plunger outwardly but not out of the tampon applicator. This approach does indeed save space and provides for discretion when carrying the embodiment herein. Nonetheless, these embodiments provide only for a plunger that must be pre-inserted into the tampon applicator. Thus, a need exists to provide embodiments, i.e., compact tampon insertion devices, in which a plunger is not substantially pre-inserted within a plunger.

SUMMARY OF THE INVENTION

Accordingly, the invention provides a tampon insertion device comprising a tampon applicator having a first end, a second end opposed to the first end, and a tampon inserted within the tampon applicator having a string attached thereto. The tampon is positioned within the tampon applicator and a plunger is attached to the tampon applicator by the tampon string. The string is attached to the plunger at at least one connection point on the plunger. Preferably, the string is substantially threaded through the plunger. The tampon applicator with the tampon therein and the plunger are preferably positioned adjacent to one-another in a substantially parallel orientation prior to the use of the tampon insertion device. Such parallel orientation between the tampon applicator and the plunger is maintained by the tampon string connected to the plunger.

In one preferred embodiment herein, the string of the tampon is already threaded through the plunger prior to use of the tampon insertion device. More specifically, the string is pre-threaded by the manufacturer. In another highly preferred embodiment, the tampon insertion device is combined with a package that encompasses the tampon insertion device such that the tampon applicator and the plunger of the tampon insertion device are positioned adjacent to one-another in a substantially parallel orientation.

In another embodiment herein, the tampon insertion device comprises a tampon applicator having an inner surface, an outer surface, a first end and a second end. The tampon insertion device further comprises a tampon having a string, a first side and a second side opposed to the first side thereof The tampon is positioned within the tampon applicator such that the first side of the tampon is adjacently oriented toward the first end of the tampon applicator and the second side of the tampon is adjacently oriented toward the second end of the tampon applicator.

Lastly, the tampon insertion device comprises a plunger having an inner surface, an outer surface, a first part and a second part. The plunger first part is positioned at least partially within the tampon applicator and adjacent to the second side of the tampon. The plunger first part is connected to the plunger second part by a flexible hinge. The hinge enables the tampon applicator with the tampon therein and the plunger to be positioned adjacent to one-another in a substantially parallel orientation prior to the use of the tampon insertion device without using the tampon's string.

In a preferred embodiment herein, the plunger first part is securely fixed within the tampon applicator such that the plunger first part cannot be easily removed from the normal forces associated with carrying, packing or holding the tampon insertion device. More specifically, the plunger first part is securely fixed within the tampon applicator by a locking device. The locking device herein comprises a pair of nibs positioned on the inner surface of the tampon applicator and adjacent to the second end of the tampon applicator and a pair of nibs positioned on the plunger outer surface and adjacent to the first part of the plunger such that the nibs of the tampon applicator and the nibs of the plunger first part prevent the plunger first part from unintentionally exiting the second end of the tampon applicator. Such unintentional exiting might result from gravity, awkward carrying of the tampon insertion device, dropping the tampon insertion device, etc. Also, preferably, this tampon insertion device may be packaged.

More specifically, the plunger first part is at least partially and preferably inserted within the tampon applicator. The plunger second part is the main body of the plunger and resides on the outside of the plunger. Furthermore, in this configuration, the hinge attaches the plunger first part to the plunger second part; i.e., herein, the plunger is not itself connected to the tampon applicator by the hinge. In addition, the plunger first part is preferably detachably connected to the tampon applicator by an inter-locking mechanism, e.g., the nibs mentioned above. The interlocking mechanism comprises two parts: a first lock positioned within the inner surface of the tampon applicator and oriented toward the second end of the tampon applicator and a second lock positioned on the outer surface of the plunger first part.

Essentially, the first lock detachably locks with the second lock such that the first lock and the second lock will preferably not detach during normal handling, carrying or storing of the tampon insertion device and the plunger will not unintentionally exit from the tampon applicator. By the term "detachably locks" it is meant herein that first lock and second lock will be so locked together that preferably only one, e.g., a user, directly acting upon the tampon insertion device will be able to detach the first lock from the second lock.

In another preferred embodiment herein, a tampon insertion device comprises a tampon applicator having an inner surface, an outer surface, a first end and a second end. Also, a tampon is positioned within the tampon applicator, the tampon having a first part and a second part. Lastly, a plunger is partially inserted within the tampon applicator having an inner surface, an outer surface, a first part, a second part opposed to the first part, and a flexible portion positioned between the first part and the second part, the flexible portion operating to preferably bend the plunger into a substantially parallel orientation prior to the use of the tampon insertion device; such bending being in the range from about 0° to about 180° and preferably from about 90° to about 180° and more preferably from about 120° to about 180°. The flexible portion of this plunger herein operates to affect such parallel orientation similarly to the hinge in the previous tampon insertion device.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

Figure 1:
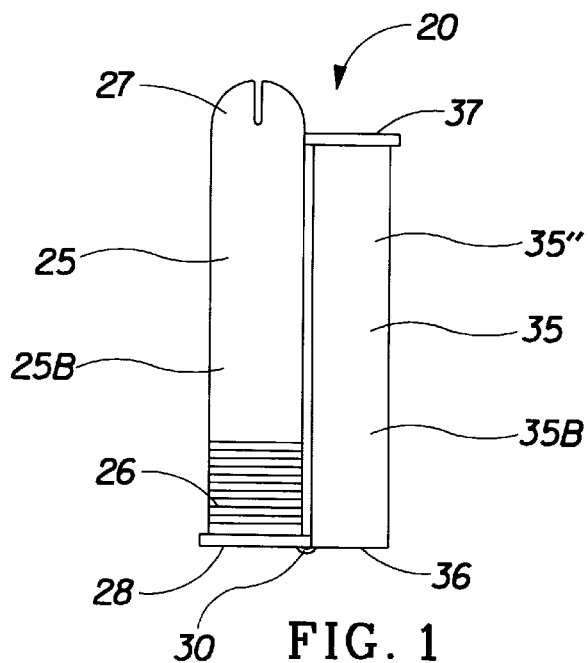
FIG. 1 is a plane view of one embodiment of the invention.

FIG. 1 provides a tampon insertion device 20 that comprises a tampon applicator 25 having an inner surface 25A (not shown), an outer surface 25B, a first end 27 and a second end 26. The tampon insertion device 20 further comprises a tampon 40 (FIG. 6) having a string 42, a first side 40A and a second side 40B. The tampon 40 is positioned within the tampon applicator 25 such that the first side 40A of the tampon 40 is adjacently oriented toward the first end 27 of the tampon applicator 25 and the second side 40B (not shown) of the tampon 40 is adjacently oriented toward the second end 26 of the tampon applicator 25. Lastly, the tampon insertion device 20 comprises a plunger 35 having an inner surface 35 A (not shown), an outer surface 35B, a first end 36 and a second end 37. The first end 36 of the plunger 35 is connected to the second end 26 of the tampon applicator 25 by a flexible hinge 30. The hinge 30 enables the tampon applicator 25 with a tampon 40 therein and the plunger 35 to be positioned adjacent to one-another in a substantially parallel orientation prior to the use of the tampon insertion device 20 without using the tampon's string 42.

Figure 2:
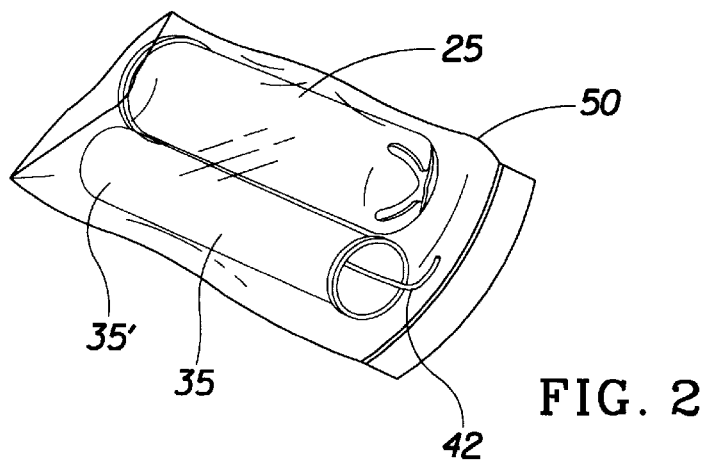
FIG. 2 is a perspective view of the embodiment of FIG. 1 encased in a package.

In FIG. 2, the tampon insertion device 20 is shown packaged in package 50.

Also, the tampon applicator 25 and plunger 35 are shown to be placed in parallel orientation to one-another in the package 50. Preferably, a tampon 40 (not shown) is positioned within the tampon applicator 25 and packed in the package 50 along with the tampon insertion device 20.

Figure 3:
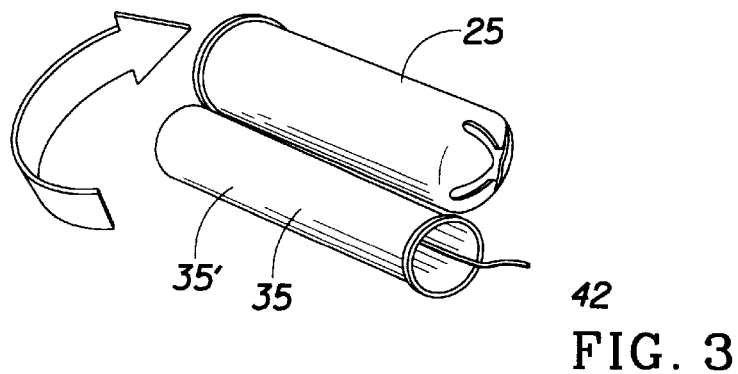
FIG. 3 is a perspective view of the embodiment of FIG. 2 without the package.
Figure 4:
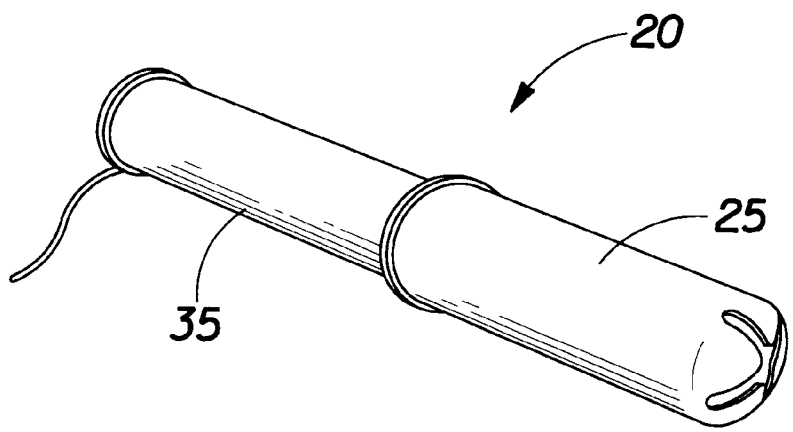
FIG. 4 is a perspective view of the embodiment of FIG. 3 showing the tampon insertion device in its expulsion position.
Figure 5:
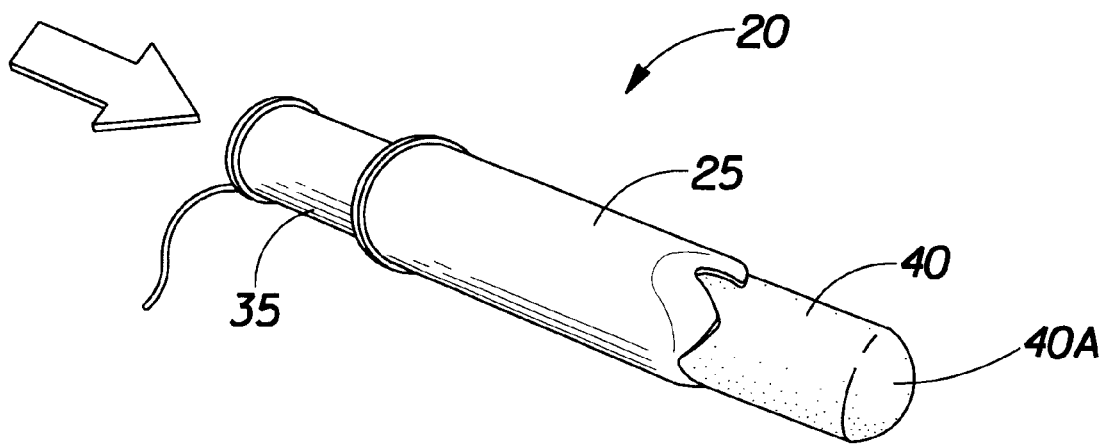
FIG. 5 is a perspective view of the embodiment of FIG. 4 showing a tampon being expelled.

FIG. 3 provides a view showing the orientation about which the plunger 35 will be moved with respect to the tampon applicator 25. More specifically, the flex hinge or hinge 30 allows the plunger 35 to be both connected to the tampon applicator 25 and also causes the plunger 35 to line up in linear orientation, i.e., the expulsion position, with the tampon applicator 25. By the term "linear orientation" or "expulsion position" it is meant herein that once activated by a user or by the natural movement of the hinge 30, the plunger 35 will be positioned linearly, i.e., in a straight line, with the tampon applicator 25 in a ready position to expel the tampon 40—please see FIG. 4.

In an alternative embodiment herein, the tampon insertion device 20 of FIG. 1 provides a plunger 35 that comprises a first part 35' and a second part 35". The plunger first part 35' is at least partially and preferably inserted within the tampon applicator 25. The plunger second part 35" is the main body of the plunger 35 and resides on the outside of the plunger 35 (FIG. 1). Furthermore, in this configuration, the hinge 30 attaches the plunger first part 35' to the plunger second part 35"; i.e., herein, the plunger 35 is not itself connected to the tampon applicator 25 by the hinge 30. In addition, the plunger first part 35' is preferably detachably connected to the tampon applicator 25 by nibs located within the tampon applicator 25 that inter-lock with the plunger first part 35' to keep it from falling out of the tampon applicator 25; i.e., such inter-locking providing the plunger first part 35' to be securely fixed within the tampon applicator 25. By the term "securely fixed" it is meant herein that the plunger first part 35', once inter-locked within the tampon applicator 25, will not be easily removed therefrom by normal forces exerted on the tampon insertion device such as carrying, holding, packing, etc.

Figure 6:
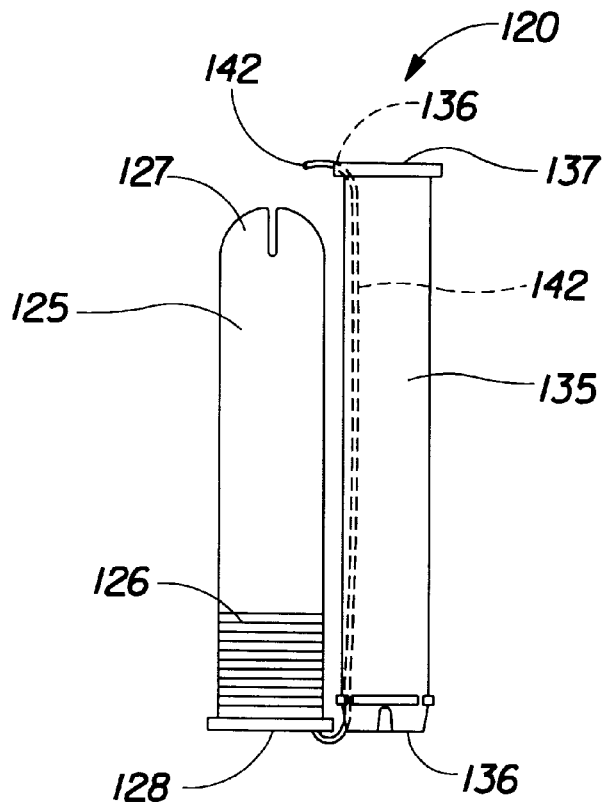
FIG. 6 is a plane view of an alternative embodiment of the invention.

As is shown in FIG. 6, the invention provides a tampon insertion device 120 comprising a tampon applicator 125 having a first end 127, a second end 126, and an opening 128. Preferably a tampon 140 (not shown) is positioned within the tampon applicator 125. Also preferably, the tampon 140 has a string 142 attached thereto.

As shown, the tampon 140 is positioned within the tampon applicator 125, and a plunger 135 is attached to the tampon applicator 125 by the tampon string 142.

The tampon string 142 is attached to the plunger 135 at at least one connection point 136 (FIG. 6) on the plunger 135. The tampon applicator 125 with the tampon 140 therein and the plunger 135 are preferably positioned adjacent to one-another in a substantially parallel orientation prior to the use of the tampon insertion device 120. Such parallel orientation between the tampon applicator 125 and the plunger 135 is maintained by the tampon string 142 being connected to the plunger 135 at the connection point 138.

Figure 7:
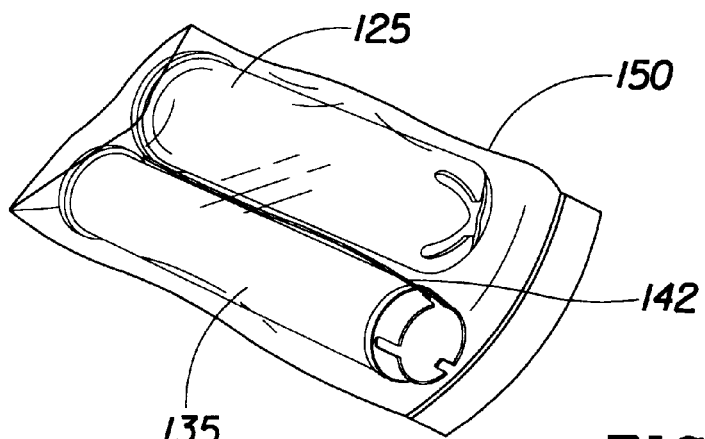
FIG. 7 is a perspective view of the embodiment of FIG. 6 encased in a package.

The connection point 138 may be located at either the first end 136 or the second end 137 of the plunger 135. Preferably, the connection 138 is positioned at the second end 137 of the plunger 135. In practice, once the plunger 135 is lined up in its correct linear orientation or expulsion position, the string 142 is removed by a user from the connection point 138. The tampon insertion device 120 is inserted within a user's vaginal cavity and the tampon 140 is expelled into the vaginal cavity by the plunger 135. After expulsion of the tampon 140, the tampon insertion device 120 is discarded. Also, in one preferred embodiment, the string 142 of the tampon 140 is already threaded through the plunger 135 prior to use of the tampon insertion device 120. More specifically, the string 142 is pre-threaded by the manufacturer. In another highly preferred embodiment, the tampon insertion device 120 is combined with a package 150 (FIG. 7) that encompasses the tampon insertion device 120 such that the tampon applicator 125 and the plunger 135 of the tampon insertion device 120 are positioned adjacent to one-another in a substantially parallel orientation.

Figures 8, 9:
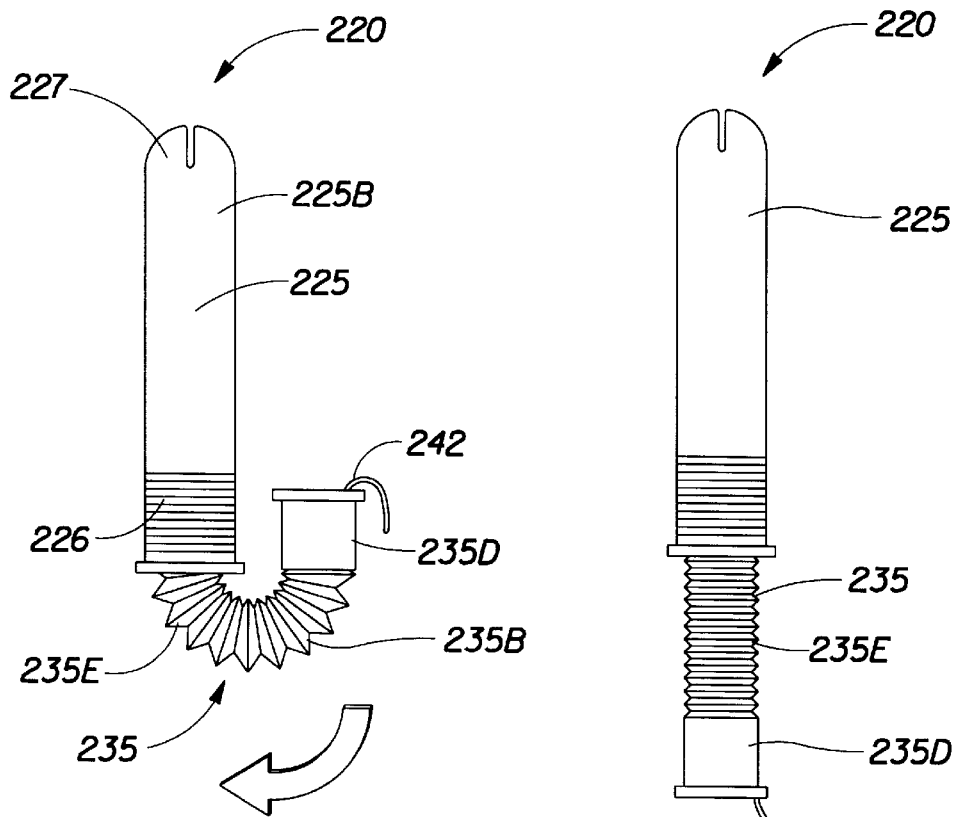
FIG. 8 is a plane view of an alternative embodiment of the invention.
FIG. 9 is a plane view of an alternative orientation of the embodiment of FIG. 8.
Figure 10:
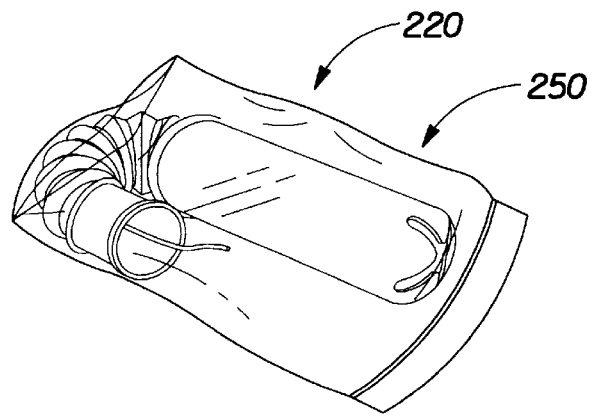
FIG. 10 is a perspective view of the embodiment of FIG. 8 encased in a package.

In another preferred embodiment shown in FIG. 8, a tampon insertion device 220 comprises a tampon applicator 225 having an inner surface 225A (not shown), an outer surface 225B, a first end 227 and a second end 226. Also, a tampon 240 is preferably positioned within the tampon applicator 225. The tampon has a first part 40A and a second part 40B opposed to the first part 40A. Lastly, a plunger 235 is at least partially inserted within the tampon applicator 225. The plunger 235 has an inner surface 235A, an outer surface 235B, a first part 235', a second part 235" opposed to the first part 235', and a flexible portion 235''' positioned between the first part 235' and the second part 235" of the plunger 235. The flexible portion 235''' operates to bend the plunger 235 into a substantially parallel orientation prior to the use of the tampon insertion device 220. The flexible portion 235''' of the plunger 235 operates to affect such parallel orientation similarly to the hinge 30 in the tampon insertion device of FIG. 1.

Preferably, the plunger first part 235' is detachably connected to the tampon applicator 220 by an inter-locking mechanism 260. In short, the inter-locking mechanism 260 comprises two parts: a first lock 262 positioned within the inner surface 225A of the tampon applicator 225 and oriented toward the second end 226 of the tampon applicator 225 and a second lock 264 positioned on the outer surface 235B of the plunger first part 235'. Essentially, the first lock 262 detachably locks with the second lock 264 such that the first lock 262 and the second lock 264 will preferably not detach during normal handling, carrying or storing of the tampon insertion device 220. By the term "detachably locks" it is meant herein that first lock 262 and second lock 264 will be so locked together that preferably only one, e.g., a user, directly acting upon the tampon insertion device 220 will be able to detach the first lock 262 from the second lock 264.

The disclosures of all patents, patent applications (and any patents which issue thereon, as well as any corresponding published foreign patent applications), and publications mentioned throughout this patent application are hereby incorporated by reference herein. It is expressly not admitted, however, that any of the documents incorporated by reference herein teach or disclose the present invention. It is also expressly not admitted that any of the commercially available materials or products described herein teach or disclose the present invention.

What is claimed is:

1. A tampon insertion device in combination with a tampon, comprising:

A) a tampon applicator having a first end and a second end;

B) a tampon having a string, the tampon being positioned within the tampon applicator; and C) a plunger attached to the tampon applicator by the tampon string, the string being attached to the plunger at at least one connection point, wherein the string of the tampon is already threaded through the plunger prior to use of the tampon insertion device, the tampon applicator with the tampon therein and the plunger being positioned adjacent to one-another in a substantially parallel orientation prior to the use of the tampon insertion device.

2. The tampon insertion device of claim 1 wherein the plunger is hollow.

3. A tampon insertion device in combination with a tampon, the combination being in a package, comprising:

A) a tampon applicator having a first end and a second end;

B) a tampon having a string, the tampon being positioned within the tampon applicator;

C) a plunger attached to the tampon applicator by the tampon string, the string being attached to the plunger at at least one connection point, wherein the string of the tampon is already threaded through the plunger prior to use of the tampon insertion device; and D) a package encompassing the tampon insertion device such that the tampon applicator and the plunger of the tampon insertion device are positioned adjacent to one-another in a substantially parallel orientation.

4. The tampon insertion device of claim 3 wherein the plunger is hollow.

* * * * *